(12) United States Patent
Furuya et al.

(10) Patent No.: US 7,622,563 B2
(45) Date of Patent: Nov. 24, 2009

(54) PROCESS FOR PRODUCING GLYCOSIDE

(75) Inventors: Masayuki Furuya, Omuta (JP);
Hidetoshi Tsunoda, Sodegaura (JP);
Tsuneji Suzuki, Sodegaura (JP);
Akinori Nagatomo, Omuta (JP);
Masaru Wada, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 536 days.

(21) Appl. No.: 10/518,640

(22) PCT Filed: Jul. 11, 2003

(86) PCT No.: PCT/JP03/08820

§ 371 (c)(1),
(2), (4) Date: Dec. 20, 2004

(87) PCT Pub. No.: WO2004/007516

PCT Pub. Date: Jan. 22, 2004

(65) Prior Publication Data

US 2005/0272921 A1     Dec. 8, 2005

(30) Foreign Application Priority Data

Jul. 11, 2002    (JP) .............................. 2002-202420

(51) Int. Cl.
C07H 15/00    (2006.01)
(52) U.S. Cl. .................................. 536/18.6
(58) Field of Classification Search ................. 536/18.6
See application file for complete search history.

(56) References Cited

FOREIGN PATENT DOCUMENTS

| | | |
|---|---|---|
| JP | 62-263194 A | 11/1987 |
| JP | 62-263195 A | 11/1987 |
| JP | 63-145213 A | 6/1988 |
| JP | 1-249796 A | 10/1989 |
| JP | 5-51394 A | 3/1993 |
| JP | 6-239716 A | 8/1994 |
| JP | 2000-314084 A | 11/2000 |
| JP | 2000-319116 A | 11/2000 |
| JP | 2002-193990 A | 7/2002 |

OTHER PUBLICATIONS

March et al, General Organic & Biochemistry, 5th Ed., 1998, p. 464.*
Elly Smits et al., "Reliable method for the synthesis of aryl β-D-glucopyranosides, using boron trifluoride-diethyl ether as catalyst" Journal of the Chemical Society, Perkin Transactions 1: Organic and Bio-Organic Chemistry, 1996, pp. 2873-2877, Coden: JCPRB4, ISSN: 0300-922X.
Smits et al., "Reliable method for the synthesis of aryl β-D-glucopyranosides, using boron trifluoride-diethel ether as catalyst," J. Chem. Soc., 1996, vol. 24, pp. 2873-2877.

* cited by examiner

Primary Examiner—Patrick T Lewis
Assistant Examiner—Ganapathy Krishnan
(74) Attorney, Agent, or Firm—Buchanan Ingersoll & Rooney PC

(57) ABSTRACT

A glycoside in which at least two phenolic hydroxyl groups of a compound having at least two phenolic hydroxyl groups in its molecule are glycosidically linked to anomeric carbon atoms of at least two sugar molecules can be prepared with high yield by a method including the step of allowing phenolic hydroxyl groups of a compound having at least two phenolic hydroxyl groups in its molecule to react with sugar molecules each having an acetylated hydroxyl group attached to an anomeric carbon atom in the presence of an organic solvent and an acid catalyst while removing acetic acid formed during the reaction from the reaction system.

4 Claims, No Drawings

PROCESS FOR PRODUCING GLYCOSIDE

TECHNICAL FIELD

The present invention relates to a method for preparing a glycoside. In particular, the present invention relates to a method for preparing a glycoside in which a polyphenol is glycosidically linked to a sugar, more particularly, the present invention relates to a method for preparing a glycoside in which a gallic acid derivative is glycosidically linked to a sugar.

BACKGROUND ART

In recent years, polyphenols, which have skin whitening effects and antioxidative effects, have attracted attention. For example, gallic acid and its esters have been expected to be applied as skin whitening agents or antioxitdants in many fields, for example, external preparations for skins such as cream and milky lotions; and hair treatment agents such as hair setting agents and hair styling gel. In addition, the distinctive effect on hair properties, that is, the effect of imparting elasticity to hair has been disclosed in Japanese Unexamined Patent Application Publication No. 2000-314084.

However, such a polyphenol exhibits disadvantageous properties in that it is an irritant and causes sensitization. Furthermore, the polyphenols readily color. For example, the use of gallic acid derivatives in a formulation leads to coloration or precipitation; hence, it is difficult to sufficiently exhibit skin whitening and antioxidative effects. To prevent such coloration or precipitation of the polyphenols, a process of adding a metalloporphyrin complex and an organic reducing agent is disclosed in Japanese Unexamined Patent Application Publication No. 63-145213, and a process of adding a specific polyol alone or with an antioxidant such as ascorbic acid is disclosed in Japanese Unexamined Patent Application Publication No. 6-239716. However, these processes are still unsatisfactory.

To solve the above-described problems on such polyphenols, processes for using glycosides have been known for a long time. For example, highly toxic hydroquinone is linked with glucose to produce arbutin having a skin whitening effect. A process for using glycoside in which a sugar derivative is linked with at least one hydroxyl group among three hydroxyl groups of gallic acid is disclosed in Japanese Unexamined Patent Application Publication No. 2000-319116. This patent discloses the following process: Gallic acid or its ester reacts with a sugar having partially or fully acetylated hydroxyl groups or with a sugar halogenized at an anomeric position in a solvent to form a glycoside in the presence of an acid catalyst, for example, boron trifluoride diethyl etherate ($BF_3.Et_2O$), tin tetrachloride ($SnCl_4$), or zinc chloride ($ZnCl_2$). The resulting glycoside is deprotected, if necessary in the presence of an acid catalyst or an alkaline catalyst, then extracted and purified by column chromatography.

However, the yield achieved by the process disclosed in Japanese Unexamined Patent Application Publication No. 2000-319116 is low; hence, the process is also unsatisfactory.

Japanese Unexamined Patent Application Publication Nos. 62-263194, 62-263195, 1-249796, and 5-51394 disclose the following: A compound having one or two phenolic hydroxyl group(s) in its molecule reacts with a peracetylated sugar derivative, for example, peracetylated glucose, while removing acetic acid formed as a by-product from the reaction system by distillation, to form a compound having a glycosidic bond formed by the elimination of acetic acid generated by allowing one of the phenolic hydroxyl groups of the compound having the phenolic hydroxyl groups in its molecule to react with an acetyl group attached via an oxygen atom to an anomeric carbon atom of the peracetylated sugar derivative. However, hitherto, a process for preparing a compound having at least two glycosidic bonds formed by the elimination of acetic acid generated by allowing at least two phenolic hydroxyl groups of a compound having at least two phenolic hydroxyl groups in its molecule to react with acetyl groups each linked via an oxygen atom to an anomeric carbon atom of a peracetylated sugar derivative, for example, peracetylated glucose, and a process for preparing a glycoside with the resulting compound, have not been reported.

It is an object of the present invention to provide a method for preparing a glycoside in which at least two phenolic hydroxyl groups of a compound having at least two phenolic hydroxyl groups in its molecule are glycosidically linked to at least two sugar molecules by allowing a compound having at least two phenolic hydroxyl groups in its molecule to react with at least two sugar molecules each having an acetylated hydroxyl group attached to an anomeric carbon atom.

DISCLOSURE OF INVENTION

The inventors studied a process for glycosylating methyl gallate by allowing the methyl gallate to react with glucose pentaacetate in the presence of a solvent and a Lewis acid. In the course of the process, the inventors found the following: The presence of acetic acid formed as a by-product causes substrates and a product to be in equilibrium. A compound in which one glucose pentaacetate is glycosidically linked with one phenolic hydroxyl group of the methyl gallate is in equilibrium with a compound in which two glucose pentaacetate are glycosidically linked with two phenolic hydroxyl groups of the methyl gallate. The presence of acetic acid in the reaction system causes some of the methyl gallate molecules and some of the molecules of the compound in which one glucose pentaacetate is glycosidically linked with one phenolic hydroxyl group of the methyl gallate to undergo acetylation of the phenolic hydroxyl groups in their molecules. As a result, skeletons that cannot react with the glucose pentaacetate anymore are formed.

The inventors have conducted extensive studies based on the results, and found that, by performing the reaction while removing the acetic acid formed as a by-product from the reaction system, the yields of methyl gallate and the compound in which the two glucose pentaacetate molecules are glycosidically linked with the phenolic hydroxyl groups of the methyl gallate are significantly improved. This finding has led to the completion of the present invention.

The present invention relates to a method for preparing a glycoside in which at least two phenolic hydroxyl groups of a compound having at least two phenolic hydroxyl groups in its molecule are glycosidically linked to anomeric carbon atoms of at least two sugar molecules, the method including the step of allowing a compound having at least two phenolic hydroxyl groups in its molecule to react with at least two sugar molecules each having an acylated hydroxyl group attached to an anomeric carbon atom in the presence of an organic solvent and an acid catalyst while removing acetic acid formed during the reaction from the reaction system.

BEST MODE FOR CARRYING OUT THE INVENTION

Examples of compounds each having at least two phenolic hydroxyl groups in their molecules include, but are not limited to, the compounds represented by the following formulae (1) and (2):

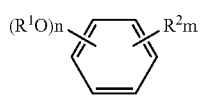

(1)

wherein, in the formula (1), R1 represents hydrogen, $C_1$-$C_{18}$ straight or branched alkyl or alkenyl, $C_1$-$C_{18}$ acyl, or optionally substituted benzyl; R2 represents hydrogen, optionally substituted $C_1$-$C_{18}$ straight or branched alkyl or alkenyl, —(C=O)—R3-R4 (wherein R3 represents $C_1$-$C_{18}$ straight or branched alkylene or alkenyl, and R4 represents optionally substituted phenyl), —R3-(C=O)R4 (wherein R3 represents $C_1$-$C_{18}$ straight or branched alkylene or alkenyl, and R4 represents optionally substituted phenyl), optionally substituted amino, optionally substituted phenyl, —O—R5, —S—R5, —S—S—R5, —NH—R5, —SO$_2$—R5, —CONH—R5, —NHCO—R5, —COO—R5, —OCO—R5, —OCONH—R5, —NHCOO—R5, —NHCONH—R5, —OCOO—R5, —SO$_2$NH—R5, or —NHSO$_2$—R5 (wherein R5 represents optionally substituted phenyl); n is an integer of 2 to 5; m is an integer of 1 to 3,

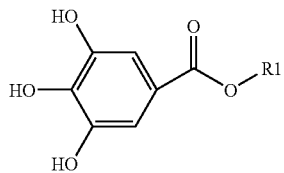

(2)

wherein, in the formula (2), R1 represents hydrogen, or $C_1$-$C_{10}$ straight or branched alkyl or alkenyl.

In the formula (1), R1 represents hydrogen, $C_1$-$C_{18}$ straight or branched alkyl or alkenyl, $C_1$-$C_{18}$ acyl, or optionally substituted benzyl.

In the formula (1), R2 represents hydrogen, optionally substituted $C_1$-$C_{18}$ straight or branched alkyl or alkenyl, —(C=O)—R3-R4 (wherein R3 represents $C_1$-$C_{18}$ straight or branched alkylene or alkenyl, and R4 represents optionally substituted phenyl), —R3-(C=O)R4 (wherein R3 represents $C_1$-$C_{18}$ straight or branched alkylene or alkenyl, and R4 represents optionally substituted phenyl), optionally substituted amino, optionally substituted phenyl, —O—R5, —S—R5, —S—S—R5, —NH—R5, —SO$_2$—R5, —CONH—R5, —NHCO—R5, —COO—R5, —OCO—R5, —OCONH—R5, —NHCOO—R5, —NHCONH—R5, —OCOO—R5, —SO$_2$NH—R5, or —NHSO$_2$—R5 (wherein R5 represents optionally substituted phenyl); n is an integer of 2 to 5; m is an integer of 1 to 3.

In the formula (1), examples of the optionally substituted benzyl groups include, for example, methylbenzyl and methoxybenzyl. Examples of the optionally substituted phenyl include phenyl substituted by $C_1$-$C_{18}$ straight or branched alkyl or alkenyl, hydroxyl, alkoxyl, benzyloxycarbonyl, carboxyl, amino, or alkyl-substituted amino. Furthermore, in the formula (1), examples of the optionally substituted amino groups include, for example, N,N'-dimethylamino, N,N'-diethylamino, and N,N'-dibutylamino.

In the formula (2), R1 represents hydrogen, or $C_1$-$C_{10}$ straight or branched alkyl or alkenyl.

Representative examples of the compound having at least two phenolic hydroxyl groups in its molecule include, for example, compounds having two phenolic hydroxyl groups, for example, catechol, resorcin, hydroquinone, β-resorcylic acid, γ-resorcylic acid, 2,4-dihydroxybenzaldehyde, 3,4-dihydroxybenzaldehyde, 2,5-dihydroxybenzaldehyde, 2,4-dihydroxyacetophenone, 3,4-dihydroxyacetophenone, and 2,5-dihydroxyacetophenone; compounds having three phenolic hydroxyl groups, for example, gallic acid and methyl gallate; compounds in which aromatic rings are linked to each other joined by, for example, alkyl, alkenyl, sulfone, and amide, for example, 1,3-bis(2,4-dihydroxyphenyl)propane, 1,3-bis(2,4-dihydroxyphenyl)-1-propanone, 1,3-bis(2,4-dihydroxyphenyl)-1-propen-3-one, 1,3-bis(2-hydroxy-4-benzyloxyphenyl)-1-propen-3-one, 1-(2,4-dihydroxyphenyl)-3-(2,4-dibenzyloxyphenyl)-1-propen-1-one, 2,2'-bis(4-hydroxyphenyl)propane, 4,4'-dihydroxydiphenylsulfone, 1,3-bis[2-(4-hydroxyphenyl)propyl]benzene, N,S-bis(4-hydroxyphenyl)sulfonamide, and N,C-bis(4-hydroxyphenyl)carboxamide; and flavonoids, for example, catechin, epicatechin, rutin, quercetin, and cyanidin. The gallic acid derivatives are preferable. Examples of the gallic acid derivatives include, but are not limited to, for example, alkyl gallates such as methyl gallate, ethyl gallate, propyl gallate, and isopropyl gallate. Among the preferred alkyl gallates are methyl gallate and ethyl gallate, which are readily available commercially.

Sugars, which are used for the present invention, having acetylated hydroxyl groups attached to anomeric carbon atoms may have, but are not limited to, partially or fully acetylated hydroxyl groups other than the hydroxyl groups attached to the anomeric carbon atoms. Examples of the sugars each having an acetylated hydroxyl group attached to an anomeric carbon atom include, for example, 1-O-acylated sugars such as 1,2,3,4,6-penta-O-acetylglucopyranose (glucose pentaacetate), 1,2,3,4,6,2',3',4',6'-nona-O-acetylmaltopyranose (maltose nonaacetate), and 1,2,3,4,6-penta-O-acetylgalactopyranose (galactose pentaacetate); and thioglycoside such as phenyl-2,3,4,6-tetra-O-acetylthioglucopyranoside. The 1-O-acylated sugars that have an excellent shelf life and that are readily activated by an acid are preferable. The glucose pentaacetate is the most preferable. These sugars each having an acetylated hydroxyl group attached to an anomeric carbon atom are commercially available. Sugars that can be easily synthesized, for example, glucose pentaacetate may be synthesized (see Example 5). Synthesized sugars each having an acetylated hydroxyl group attached to an anomeric carbon atom are isolated in a powder form and then the resulting powder may be used. Alternatively, solutions containing the sugars each having an acetylated hydroxyl group attached to an anomeric carbon atom may be used. When a 1-O-acylated sugar such as glucose pentaacetate is synthesized by allowing a sugar to react with acetic anhydride, since the reaction mixture containing the sugar having an acetylated hydroxyl group attached to an anomeric carbon atom also contains acetic acid, it is necessary to remove the acetic acid by distillation or washing before glycosidation.

In sugars, an α-anomer and a β-anomer are generally present as isomers for the pyranose forms. Each of the anomers may be used in the present invention alone. A mixture of an α-anomer and a β-anomer may also be used. The β-anomer is preferable due to its high reactivity. When a β-anomer is used in the reaction described above, part of the β-anomer is isomerized to its α-anomer, while when a mixture of α-anomer and β-anomer is used, the isomerization from the β-anomer to the α-anomer tends to be slightly suppressed.

The amount of sugar used having an acetylated hydroxyl group attached to an anomeric carbon atom for the reaction with the compound having at least two phenolic hydroxyl groups in its molecule is not limited, provided that the reaction sufficiently proceeds. The amount of sugar used is generally equal to ten times, preferably 1.1 to 5 times the total molar amount of the phenolic hydroxyl groups of the compound having at least two phenolic hydroxyl groups. The amount of sugar less than this range means not only a stoichiometric deficiency, but also results in the undesired decrease of the reaction rate and the yield. Therefore, an amount of sugar less than this range is not preferable. In the case where the amount of sugar is above this range, the yield is not improved. In addition, it tends to be difficult to perform any subsequent operations, i.e., isolation operation, for example, filtration, due to high viscosity of the reaction mixture. Therefore, an amount of sugar above this range is also not preferable.

Organic solvents other than acetic acid may be used for the reaction of the phenolic hydroxyl groups of the compound having at least two phenolic hydroxyl groups with the sugar molecules each having an acetylated hydroxyl group attached to an anomeric carbon atom. The organic solvents used are not limited, provided that the organic solvents are inert toward the compounds having at least two phenolic hydroxyl groups, the sugar molecules each having an acetylated hydroxyl group attached to an anomeric carbon atom, and the product prepared by the reaction between them. Examples of the organic solvents include, for example, aromatic hydrocarbons such as benzene, toluene, (mixed) xylene(s), ethylbenzene, mesitylene, trimethylbenzene, and styrene; aliphatic hydrocarbons such as pentane, hexane, cyclohexane, heptane, octane, nonane, decane, and α-pinene; halogenated hydrocarbons such as dichloromethane, dibromomethane, 1,2-dichloroethane, 1,3-dibromoethane, monochlorobenzene, o-dichlorobenzene, p-dichlorobenzene, monobromobenzene, dibromobenzene, fluorobenzene, and difluorobenzene; nitro hydrocarbons such as nitromethane, nitroethane, and nitrobenzene; esters such as methyl acetate, ethyl acetate, butyl acetate, methyl propionate, ethyl propionate, butyl propionate, methyl butyrate, ethyl butyrate, and butyl butyrate; ethers such as dimethyl ether, diethyl ether, ethyl methyl ether, ethylene glycol dimethyl ether, ethylene glycol diethyl ether, diethylene glycol dimethyl ether, diethylene glycol diethyl ether, triethylene glycol dimethyl ether, triethylene glycol diethyl ether, tetrahydrofuran, dioxane, anisole, and phenetole; ketones such as acetone, methyl ethyl ketone, methyl isobutyl ketone, and diisobutyl ketone; nitrogen-containing polar solvents such as acetonitrile, dimethylformamide, dimethylacetamide, N-methylpyrrolidone, and 1,3-dimethylimidazolidinone; sulfur-containing polar solvents such as dimethyl sulfoxide, and sulfolane; and cyclic tertiary amines such as pyridine, N-methylmorpholine, 2-picoline, 3-picoline, and 4-picoline. Among the compounds described above, toluene, (mixed) xylene(s), ethylbenzene, styrene, hexane, heptane, octane, α-pinene, nitroethane, dioxane, pyridine, 2-picoline, 3-picoline, and 4-picoline, which form azeotropes with acetic acid, are preferable. In view of high azeotropic composition, ease of handling, and price, xylene, octane, and ethylbenzene are more preferable. These organic solvents may be used alone or in combination.

The amount of organic solvent used for the reaction of the phenolic hydroxyl groups of the compound having at least two phenolic hydroxyl groups in its molecule with the sugar molecules each having an acetylated hydroxyl group attached to an anomeric carbon atom is, but are not limited to, an amount such that the substrate concentration is usually 2 percent to 70 percent by weight, preferably 5 percent to 50 percent by weight. In the case of more than 50 percent by weight, it is uneconomical due to low volumetric efficiency, while at less than five percent by weight, the viscosity of slurry is high, thus increasing the load on a stirrer.

Examples of acid catalysts used for the reaction of the phenolic hydroxyl groups of the compound having at least two phenolic hydroxyl groups in its molecule with the sugar molecules each having an acetylated hydroxyl group attached to an anomeric carbon atom include, but are not limited to, for example, protonic acids and Lewis acids, which are commonly used for organic syntheses. Examples of the protonic acids include, for example, mineral acids such as hydrochloric acid, hydrogen bromide, hydrogen fluoride, sulfuric acid, nitric acid, and phosphoric acid; and sulfonic acids such as methanesulfonic acid, p-toluenesulfonic acid, and trifluoromethanesulfonic acid. Examples of the Lewis acids include, for example, boron trifluoride ($BF_3$), zinc dichloride ($ZnCl_2$), zinc tetrachloride ($ZnCl_4$), iron trichloride ($FeCl_3$), tin dichloride ($SnCl_2$), tin tetrachloride ($SnCl_4$), titanium tetrachloride ($TiCl_4$), tin tetrachloride ($SnCl_4$), and magnesium dichloride ($MgCl_2$). These acid catalysts may be used alone or in combination. Among these acid catalysts described above, the Lewis acids that can react under mild conditions are preferable. Boron trifluoride is more preferable in view of solubility and activity. Boron trifluoride complexes, for example, an ether complex, an acetic acid complex, a methanol complex, and a phenol complex may also be used.

The amount of acid catalyst used is determined depending on the acid catalyst used for the reaction. The amount of acid catalyst is usually 2 to 50 mole percent, preferably 5 to 40 mole percent, more preferably 10 to 30 mole percent relative to the total molar amount of the phenolic hydroxyl groups in the compound having at least one phenolic hydroxyl group in its molecule. When the amount of catalyst used is less than this range, the catalyst is ineffective; hence, the reaction rate is low, while when more than this range, the reaction rate cannot be improved, in addition, it tends to decrease the yield of the glycoside.

Examples of methods for adding the acid catalysts include, but are not limited to, for example, a step of adding a predetermined amount of the acid catalyst at the beginning of the reaction in a single operation and a step of adding a predetermined amount of the acid catalyst stepwise during the reaction. The acid catalyst is dissolved in a solvent or diluted with a solvent described above and then may be successively added dropwise. When a suspension is used in which a 1-O-acylated sugar is partially dissolved, for example, a suspension of synthesized glucose pentaacetate, in order to control the rate of formation of acetic acid at the initial stage of the reaction, the amount of catalyst added to the reaction system before reacting is preferably less than the predetermined amount. The decreased amount of catalyst is usually 2 to 10 mole percent relative to the molar amount of the phenolic hydroxyl group. After that, the remaining catalyst may be added stepwise or in a single operation until the total amount of the catalyst used reaches a predetermined amount.

The reaction temperature during the reaction of the phenolic hydroxyl groups of the compound having at least two phenolic hydroxyl groups in its molecule with the sugar molecules each having an acetylated hydroxyl group attached to an anomeric carbon atom is not limited, provided that a desired product can be produced at the temperature. The temperature is determined depending on a starting material, a catalyst, and an organic solvent. The temperature is usually 0° C. to 100° C., preferably 20° C. to 80° C., more preferably 30° C. to 60° C. At a temperature of less than 0° C., it is uneconomical because of the very low reaction rate, while at a temperature of more than 100° C., the reaction rate increases, but it tends to decrease the yield of glycoside.

The pressure during the reaction of the phenolic hydroxyl groups of the compound having at least two phenolic hydroxyl groups in its molecule with the sugar molecules each having an acetylated hydroxyl group attached to an anomeric carbon atom is not limited, provided that a desired product can be produced at the pressure. The pressure is determined in the same way as for the temperature. The pressure is usually atmospheric to 133.3 Pa (atmospheric to 1 mmHg). To control the temperature range described above, the reaction system may be maintained at a reduced pressure depending on the organic solvent used.

In a method for preparing a glycoside according to the present invention, the method includes the step of allowing a compound having at least two phenolic hydroxyl groups in its molecule to react with sugar molecules each having an acetylated hydroxyl group attached to an anomeric carbon atom in the presence of an organic solvent and an acid catalyst while removing acetic acid formed during the reaction from the reaction system. The yield of the glycoside is significantly improved by the step.

Examples of steps for removing acetic acid formed in the reaction system include, but are not limited to, for example, a substep of adjusting the concentration of substrates within a predetermined range by adding an equivalent amount of an organic solvent distilled off while removing the acetic acid with the organic solvent at a predetermined temperature by azeotropic distillation. The solvent may be successively distilled off from the reaction system and successively added to the reaction system. Alternatively, a certain amount of the solvent may be distilled off and then a certain amount of the solvent may be added. Quick removal of the acetic acid from the reaction system is preferable. In removing the acetic acid with the organic solvent from the reaction system, a high distillation rate readily causes the shift of the azeotropic composition; hence, a reactor equipped with a distillation column filled with a packing material is preferably used. The distillation rate, which is determined depending on the organic solvent used, is usually 10 to 1000 g/hr, preferably 20 to 500 g/hr relative to one mol of the compound having at least two phenolic hydroxyl groups in its molecule.

When the above-described operation is performed, the concentration of acetic acid in the reaction system is maintained at 1.0 percent by weight or less during the reaction.

When a suspension is used in which a 1-O-acylated sugar is partially dissolved, for example, a suspension of synthesized glucose pentaacetate, it is necessary to increase the distillation rate in the initial stage of the reaction (for about three hours after starting the reaction). The increased distillation rate is usually two to four times the above-described distillation rate.

The above-described reaction provides a compound that has two glycosidic linkages between two oxygen atoms of two phenolic hydroxyl groups of a compound having at least two phenolic hydroxyl groups in its molecule and anomeric carbon atoms of sugar molecules each having an acetylated hydroxyl group attached to an anomeric carbon atom.

A compound having at least two phenolic hydroxyl groups is combined with sugar molecules each having an acetylated hydroxyl group attached to an anomeric carbon atom to form a variety of compounds in which the oxygen atoms of the phenolic hydroxyl groups are linked with the anomeric carbon atoms of the sugar molecules each having an acetylated hydroxyl group attached to an anomeric carbon atom. The resulting compounds are represented by the following formula (3):

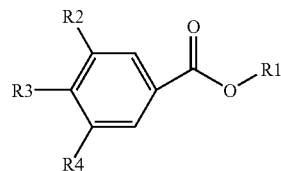

wherein, in the formula (3), R1 represents hydrogen, or $C_1$ to $C_{10}$ straight or branched alkyl or alkenyl; two of R2, R3, and R4 each represent a monosaccharide residue, a disaccharide residue, or an oligosaccharide residue, these residues each optionally having a hydroxyl group that may be acetylated or having an acetyl protective group, the remaining functional group other than the two of R2, R3, and R4 representing hydroxyl.

In the formula (3), R1 represents hydrogen, or $C_1$ to $C_{10}$ straight or branched alkyl or alkenyl; two of R2, R3, and R4 each represent a monosaccharide residue, a disaccharide residue, or an oligosaccharide residue, these residues each optionally having a hydroxyl group that may be acetylated or having an acetyl protective group, the remaining functional group other than the two of R2, R3, and R4 representing hydroxyl.

Examples of the compounds having at least two glycosidic bonds formed by the elimination of acetic acid generated by allowing at least two phenolic hydroxyl groups of a compound having at least two phenolic hydroxyl groups in its molecule to react with acetyl groups each linked via an oxygen atom to an anomeric carbon atom of a sugar molecule that has an acetylated hydroxyl group attached to an anomeric carbon atom include, for example, di(2,3,4,6-tetra-O-acetylglucosyl)hydroquinone, di(2,3,4,6-tetra-O-acetylglucosyl)resorcin, di (2,3,4,6-tetra-O-acetylglucosyl)catechol, 2,4-di(2,3,4,6-tetra-O-acetylglucosyl)-γ-resorcylic acid, 2,4-dihydroxybenzaldehyde-2,4-di(2,3,4,6-tetra-O-acetylglucoside), 2,4-dihydroxyacetophenone-2,4-di(2,3,4,6-tetra-O-acetylglucoside), 1,3-bis[2-(2,3,4,6-tetra-O-acetylglucosyloxy)-4-hydroxyphenyl]propane, 1,3-bis[2-hydroxy-4-(2,3,4,6-tetra-O-acetylglucosyloxy)phenyl]propane, 1,3-bis[2-(2,3,4,6-tetra-O-acetylglucosyloxy)-4-hydroxyphenyl]-1-propanone, 1,3-bis[2-hydroxy-4-(2,3,4,6-tetra-O-acetylglucosyloxy)phenyl]-1-propanone, 1,3-bis[2-(2,3,4,6-tetra-O-acetylglucosyloxy)-4-hydroxyphenyl]-1-propen-3-one, 1,3-bis[2-hydroxy-4-(2,3,4,6-tetra-O-acetylglucosyloxy)phenyl]-1-propen-3-one, 1,3-bis[2-(2,3,4,6-tetra-O-acetylglucosyloxy)-4-benzyloxyphenyl]propane, 1,3-bis[2-benzyloxy-4-(2,3,4,6-tetra-O-acetylglucosyloxy)phenyl]propane, 1,3-bis[2-(2,3,4,6-tetra-O-acetylglucosyloxy)-4-benzyloxyphenyl]-1-propanone, 1,3-bis[2-benzyloxy-4-(2,3,4,6-tetra-O-acetylglucosyloxy)phenyl]-1-propanone, 1,3-bis[2-(2,3,4,6-tetra-O-acetylglucosyloxy)-4-benzyloxyphenyl]-1-propen-3-one, 1,3-bis[2-benzyloxy-4-(2,3,4,6-tetra-O-acetylglucosyloxy)phenyl]-1-propen-3-one, 1-[2,4-di(2,3,4,6-tetra-O-acetylglucosyloxy)phenyl]-3-(2,4-dihydroxyphenyl)propane, 1-[2,4-di(2,3,4,6-tetra-O-acetylglucosyloxy)phenyl]-3-(2,4-dibenzyloxyphenyl)propane, 1-(2,4-dihydroxyphenyl)-3-[2,4-di(2,3,4,6-tetra-O-acetylglucosyloxy)phenyl]propane, 1-(2,4-dibenzyloxyphenyl)-3-[2,4-di(2,3,4,6-tetra-O-acetylglucosyloxy)phenyl]propane, 1-[2,4-di(2,3,4,6-tetra-O-acetylglucosyloxy)phenyl]-3-(2,4-dihydroxyphenyl)-1-propanone, 1-[2,4-di(2,3,4,6-tetra-O-acetylglucosyloxy)phenyl]-3-(2,4-dibenzyloxyphenyl)-1-propanone, 1-(2,4- dihydroxyphenyl)-3-[2,4-di(2,3,4,6-tetra-O-acetylglucosyloxy)phenyl]-1-propanone, 1-(2,4-dibenzyloxyphenyl)-3-[2,4-di(2,3,4,6-tetra-O-acetylglucosyloxy)phenyl]-1-propanone, 1-[2,4-di(2,3,4,6-tetra-O-acetylglucosyloxy)phenyl]-3-(2,4-dihydroxyphenyl)-1-propen-3-one, 1-[2,4-di(2,3,4,6-tetra-O-acetylglucosyloxy)phenyl]-3-(2,4-dibenzyloxyphenyl)-1-propen-3-one, 1-(2,4-dihydroxyphenyl)-3-[2,4-di(2,3,4,6-tetra-O-acetylglucosyloxy)phenyl]-1-propen-3-one, 1-(2,4-dibenzyloxyphenyl)-3-[2,4-di(2,3,4,6-tetra-O-acetylglucosyloxy)phenyl]-1-propen-3-one, 2-(4-hydroxyphenyl)-2'-[4-(2,3,4,6-tetra-O-acetylglucosyloxy)phenyl]propane, 2-[4-(2,3,4,6-tetra-O-acetylglucosyloxy)phenyl]-2'-(4-hydroxyphenyl)propane, 4,4'-di(2,3,4,6-tetra-O-acetylglucosyloxy)diphenylsulfone, gallic acid-3,5-bis(2,3,4,6-tetra-O-acetylglucoside), gallic acid-3,4-bis(2,3,4,6-tetra-O-acetylglucoside), gallic acid methyl ester-3,5-bis(2,3,4,6-tetra-O-acetylglucoside), gallic acid methyl ester-3,4-bis(2,3,4,6-tetra-O-acetylglucoside), gallic acid ethyl ester-3,5-bis(2,3,4,6-tetra-O-acetylglucoside), gallic acid ethyl ester-3,4-bis(2,3,4,6-tetra-O-acetylglucoside), gallic acid propyl ester-3,5-bis(2,3,4,6-tetra-O-acetylglucoside), gallic acid propyl ester-3,4-bis(2,3,4,6-tetra-O-acetylglucoside), gallic acid-3,5-bis(2,3,4,6,2',3',4',6'-octa-O-acetylmaltoside), gallic acid-3,4-bis(2,3,4,6,2',3',4',6'-octa-O-acetylmaltoside), gallic acid methyl ester-3,5-bis(2,3,4,6,2',3',4',6'-octa-O-acetylmaltoside), gallic acid methyl ester-3,4-bis(2,3,4,6,2',3',4',6'-octa-O-acetylmaltoside), gallic acid ethyl ester-3,5-bis(2,3,4,6,2',3',4',6'-octa-O-acetylmaltoside), gallic acid ethyl ester-3,4-bis(2,3,4,6,2',3',4',6'-octa-O-acetylmaltoside), gallic acid propyl ester-3,5-bis(2,3,4,6,2',3',4',6'-octa-O-acetylmaltoside), gallic acid propyl ester-3,4-bis(2,3,4,6,2',3',4',6'-octa-O-acetylmaltoside), gallic acid-3,5-bis(2,3,4,6-tetra-O-acetylgalactoside), gallic acid-3,4-bis(2,3,4,6-tetra-O-acetylgalactoside), gallic acid methyl ester-3,5-bis(2,3,4,6-tetra-O-acetylgalactoside), gallic acid methyl ester-3,4-bis(2,3,4,6-tetra-O-acetylgalactoside), gallic acid ethyl ester-3,5-bis(2,3,4,6-tetra-O-acetylgalactoside), gallic acid ethyl ester-3,4-bis(2,3,4,6-tetra-O-acetylgalactoside), gallic acid propyl ester-3,5-bis(2,3,4,6-tetra-O-acetylgalactoside), and gallic acid propyl ester-3,4-bis(2,3,4,6-tetra-O-acetylgalactoside).

The inventors found that gallic acid methyl ester-3,5-bis(2,3,4,6-tetra-O-acetylglucoside) was prepared as a main product by allowing methyl gallate, which has at least two phenolic hydroxyl groups in its molecule, to react with glucose pentaacetate, which is a sugar having an acetylated hydroxyl group attached to an anomeric carbon atom, by employing the method described above. That is, the method of the present invention is useful for preparing, from a compound represented by the formula (2), a glycoside in which hydroxyl groups at the 3-position and 5-position of a compound represented by the formula (2) are glycosidically linked with anomeric carbon atoms of sugar molecules, the sugars being, for example, monosaccharides such as glucose or galactose; disaccharides such as maltose; or oligosaccharides.

A compound prepared by the reaction described above, i.e., the compound having at least two glycosidic bonds formed by the elimination of acetic acid generated by allowing phenolic hydroxyl groups of a compound having at least two phenolic hydroxyl groups in its molecule to react with acetyl groups each linked via an oxygen atom to an anomeric carbon atom of a sugar molecule having an acetylated hydroxyl group attached to an anomeric carbon atom usually precipitates as crystals from the reaction mixture by cooling, and then the resulting crystals are separated by a solid-liquid separating operation, for example, filtration or centrifugation. When the compound cannot be precipitated from the reaction mixture as crystals by only cooling, it can be precipitated as crystals by adding a solvent in which the compound hardly dissolves, i.e., poor solvent, to the reaction mixture.

In a compound prepared by the reaction described above, that is, in the compound having at least two glycosidic bonds formed by the elimination of acetic acid generated by allowing phenolic hydroxyl groups of a compound having at least two phenolic hydroxyl groups in its molecule to react with acetyl groups each linked via an oxygen atom to an anomeric carbon atom of a sugar molecule having an acetylated hydroxyl group attached to an anomeric carbon atom, when the sugar residues have acetyl or benzoyl groups functioning as protecting groups to protect the hydroxyl groups, the compound, i.e., glycoside can be prepared by removing the protecting groups. The acetyl or benzoyl groups in the compound can be readily eliminated under basic conditions. To remove the protecting groups, for example, sodium methoxide/methanol, sodium ethoxide/ethanol, sodium hydroxide/water, potassium hydroxide/water, sodium hydroxide/aqueous methanol, or potassium hydroxide/aqueous methanol is used. In view of the solubility of the glycoside and economy, sodium hydroxide/aqueous methanol is preferable. Aqueous methanol containing 20 percent to 90 percent by weight of methanol is used.

A glycoside prepared by the method of the present invention usually precipitates from the reaction mixture, which is obtained by the reaction for removing the protecting groups described above, as crystals of the glycoside by cooling, and then the resulting crystals are separated by a solid-liquid separating operation, for example, filtration or centrifugation. When the glycoside cannot precipitate from the reaction mixture as crystals by only cooling, it can be precipitated as crystals by adding a solvent in which the compound hardly dissolves to the reaction mixture.

Among glycosides prepared by the method of the present invention, for example, gallic acid-3,5-diglucoside, gallic acid methyl ester-3,5-diglucoside, gallic acid ethyl ester-3,5-diglucoside, gallic acid propyl ester-3,5-diglucoside, gallic acid-3,5-dimaltoside, gallic acid methyl ester-3,5-dimaltoside, gallic acid ethyl ester-3,5-dimaltoside, gallic acid propyl ester-3,5-dimaltoside, gallic acid-3,5-digalactoside, gallic acid methyl ester-3,5-digalactoside, gallic acid ethyl ester-3,5-digalactoside, and gallic acid propyl ester-3,5-digalactoside, are useful due to their skin whitening effects and antioxidative effects.

Furthermore, for example, gallic acid-3,5-diglucoside, gallic acid methyl ester-3,5-diglucoside, gallic acid ethyl ester-3,5-diglucoside, gallic acid propyl ester-3,5-diglucoside, gallic acid-3,5-dimaltoside, gallic acid methyl ester-3,5-dimaltoside, gallic acid ethyl ester-3,5-dimaltoside, gallic acid propyl ester-3,5-dimaltoside, gallic acid-3,5-digalactoside, gallic acid methyl ester-3,5-digalactoside, gallic acid ethyl ester-3,5-digalactoside, and gallic acid propyl ester-3,5-digalactoside, are useful for cosmetics and hair conditioners.

These compounds include α-anomer and β-anomer, both of which can be used for these applications.

A glycoside prepared by the method of the present invention may be dried without further treatment or may be subjected to deprotection or derivatization, if necessary.

In a glycoside prepared by the method of the present invention, for example, alkyl esters attached to the gallic acid skeleton can be deprotected under basic or acidic conditions. To deprotect the alkyl esters, sodium methoxide/methanol, sodium ethoxide/ethanol, sodium hydroxide/water, potassium hydroxide/water, sodium hydroxide/aqueous methanol, potassium hydroxide/aqueous methanol, aqueous sulfuric acid, or aqueous hydrochloric acid are used.

After removing the protecting groups of a compound prepared by the glycosidation according to the present invention, the resulting glycoside is precipitated by concentration or cooling, and can then be separated by a solid-liquid separating operation. Inorganic compounds formed by deprotection can be removed by, for example, recrystallization or ion exchange.

The present invention will now be described in detail based on examples, however, the present invention is not limited to these examples.

Compounds prepared in Examples and Comparative examples are analyzed by high-performance liquid chromatography, and then the yields are determined by a calibration curve method. The analytical conditions for each compound are described below.

(1) Analytical conditions for gallic acid methyl ester-3,5-bis(2,3,4,6-tetra-O-acetylglucoside).
Column: Octadecylsilyl (ODS) column (A-312 manufactured by YMC Co., Ltd.)
Detection: Ultraviolet (UV) (240 nm)
Eluent: Methanol/water/octyl sodium sulfate=(2000 ml)/(1000 ml)/(1.0 g)
Sample preparation: The entire reaction mass is placed in a 10-ml volumetric flask, and 0.3 ml of acetic anhydride and 0.2 ml of pyridine are added to the compound, followed by heating at 40° C. for five minutes. The flask is then filled to 10 ml.

(2) Analytical conditions for gallic acid-3,5-diglucoside.
Column: Octadecylsilyl (ODS) column (A-312 manufactured by YMC Co., Ltd.)
Detection: Ultraviolet (UV) (240 nm)
Eluent: Methanol/water/octyl sodium sulfate=(20 ml)/(980 ml)/(0.8 g)
Sample preparation: A weighed quantity (about 50 mg) of the sample is dissolved in water, then the flask is filled to 10 ml.

(3) Analytical conditions for hydroquinone-1-(2,3,4,5-tetra-O-acetylglucoside) and hydroquinone-1,4-bis(2,3,4,5-tetra-O-acetylglucoside).
Column: Octadecylsilyl (ODS) column (A-312 manufactured by YMC Co., Ltd.)
Detection: Ultraviolet (UV) (230 nm)
Eluent: Acetonitrile/water=(500 ml)/(500 ml) (pH adjusted to 4 by the addition of acetic acid.)
Sample preparation: The entire reaction mass is placed in a 10-ml volumetric flask, and 0.3 ml of acetic anhydride and 0.2 ml of pyridine are added to the compound, followed by heating at 40° C. for five minutes. The flask is then filled to 10 ml.

EXAMPLE 1

To a reactor were fed 36.8 g (0.2 mol) of gallic acid methyl ester (hereinafter referred to as "GM"), 226.4 g (0.58 mol) of pentaacetyl-β-D-glucose (hereinafter referred to as "β-PAG"), and 530 g of mixed xylenes, and then 4.4 g (15 mole percent relative to the GM) of boron trifluoride diethyl etherate was added. The reaction was performed at a temperature of 43° C. to 47° C. under a pressure of 4.0 kPa to 3.6 kPa (30 mmHg to 27 mmHg) for 16 hours. During the reaction, 2.0 g of boron trifluoride diethyl etherate was further added. A distillate was successively collected. The total weight of the distillate was 440 g after 16 hours. The distillate contained 20.8 g of acetic acid. During the reaction, 150 g and 73 g of the mixed xylenes were further added at 6 and 12 hours, respectively, after starting the reaction. After finishing the reaction, the analysis of the resulting reaction mass indicated that the yield of gallic acid methyl ester-bis(2,3,4,6-tetra-O-acetylglucoside) was 91.5% based on the GM. The resulting reaction mass was cooled to room temperature to form crystals and the pressure in the reactor was increased to atmospheric pressure. The crystals were filtered and washed twice with 56 g of xylene, followed by drying, to give 155.6 g of 3,5-bis(2,3,4,6-tetra-O-acetylglucosyloxy)gallic acid methyl ester. The purity and corrected yield based on the purity were 94.5% and 87.1%, respectively. The concentration of the acetic acid was 0.32 percent to 0.38 percent by weight during the reaction.

EXAMPLE 2

To a reactor were fed 110.5 g (0.6 mol) of GM, 679.2 g (1.74 mol) of β-PAG, and 1800 g of mixed xylenes, and then 12.77 g (15 mole percent relative to the GM) of boron trifluoride diethyl etherate was added. The reaction was performed at a temperature of 43° C. to 47° C. under a pressure of 4.0 kPa to 3.6 kPa (30 mmHg to 27 mmHg) for 16 hours. After 7.45 g of boron trifluoride diethyl etherate was further added, the reaction was further performed for 2 hours. A distillate was successively collected. The total weight of the distillate was 1500 g after 18 hours. During the reaction, 509.4 g and 247.9 g of the mixed xylenes were further added at 6 and 12 hours, respectively, after starting the reaction. After finishing the reaction, the analysis of the resulting mixture indicated that the yield of gallic acid methyl ester-bis(2,3,4,6-tetra-O-acetylglucoside) was 87.1% based on the GM. The resulting mixture was cooled to room temperature to form crystals and the pressure in the reactor was increased to atmospheric pressure. The crystals were filtered and washed twice with 165 g of xylene, followed by drying, to provide 471.7 g of gallic acid methyl ester-3,5-bis(2,3,4,6-tetra-O-acetylglucoside). The purity was 92.5%. The corrected yield based on the purity was 86.1% (relative to GM). The concentration of acetic acid was 0.48 percent to 0.50 percent by weight during the reaction.

Next, 204.1 g (2.5 mol) of 49% aqueous sodium hydroxide was added dropwise over a period of four hours to a flask containing 490 g of methanol and 311.5 g of water. From five minutes after starting the dropwise addition of the aqueous sodium hydroxide, a slurry made by mixing the resulting 228.3 g (0.25 mol) of gallic acid methyl ester-bis(2,3,4,6-tetra-O-acetylglucoside) with 490 g of methanol was also added dropwise over a period of four hours to the same flask at a temperature of 10° C. to 15° C., thus causing the hydrolysis of acetyl groups functioning as protecting groups. After aging at the same temperature for one hour, the resulting crystals were filtered and washed twice with 228 g of aqueous methanol to give 343.7 g of gallic acid methyl ester-diglucoside sodium salt (undried). The resulting salt was dissolved in 215 g of water. The solution was heated to 60° C., and then 21.3 g of 49% aqueous sodium hydroxide (0.26 mol) was added dropwise over a period of two hours to hydrolyze the methyl ester. The temperature was further increased, to distill off methanol formed by the hydrolysis, thus providing 570.0 g of an aqueous solution of gallic acid-3,5-diglucoside disodium salt. The concentration of the gallic acid-3,5-diglucoside disodium salt was 22.2 percent by weight. Water was added to the disodium salt solution to adjust the concentration of the gallic acid-3,5-diglucoside disodium salt to 5.4 percent by weight. The solution was passed through a column packed with a strongly acidic ion-exchange resin in which hydrogen ions are substituted for sodium ions (LEWATIT® Type-S), and then the resulting solution was concentrated at 60° C. under reduced pressure to 35 percent by weight of gallic acid-3,5-diglucoside and cooled to 5° C. and maintained at the same temperature for two hours. The crystal precipitate was filtered and washed with water, followed by drying at 75° C., to give 92.8 g of gallic acid-3,5-diglucoside in the form of white crystals. The purity was 96.2%. The corrected yield based on the purity was 72.2% (relative to GM).

EXAMPLE 3

To a reactor were fed 39.6 g (0.2 mol) of gallic acid ethyl ester (hereinafter referred to as "GE"), 226.4 g (0.58 mol) of β-PAG, and 530 g of mixed xylenes, and then 4.4 g (15 mole percent relative to the GM) of boron trifluoride diethyl etherate was added. The reaction was performed at a temperature of 43° C. to 47° C. under a pressure of 4.0 kPa to 3.6 kPa (30 mmHg to 27 mmHg). After 10 hours, the analysis of the resulting mixture indicated that the yield of gallic acid methyl ester-3,5-bis(2,3,4,6-tetra-O-acetylglucoside) was 80.5% based on the GE. The concentration of acetic acid was 0.70 percent to 0.74 percent by weight during the reaction.

EXAMPLE 4

To a reactor were fed 18.42 g (0.10 mol) of GM, 141.7 g (0.363 mol) of the powder mixture of pentaacetyl-α-D-glucose (α-PAG) and pentaacetyl-β-D-glucose (β-PAG), the ratio of α-PAG to β-PAG being 2:8, and 300 g of mixed xylenes, and then 2.83 g (15 mole percent relative to the GM) of a boron trifluoride-acetic acid complex (boron trifluoride content: 36%) was added. The reaction was performed at a temperature of 43° C. to 47° C. under a pressure of 4.0 kPa to 3.6 kPa (30 mmHg to 27 mmHg) for 16 hours. At 12 hours after starting the reaction, 1.32 g of a boron trifluoride-acetic acid complex was further added. The xylenes were distilled off to collect 317 g after 16 hours in total. During the reaction, 85 g and 41 g of the mixed xylenes were further added at 6 and 12 hours, respectively, after starting the reaction. The yield of gallic acid methyl ester-3,5-bis(2,3,4,6-tetra-O-acetylglucoside) was 89.3% relative to GM. The concentration of acetic acid was 0.73 percent to 0.75 percent by weight in the reaction system during the reaction. Subsequently, the operation as in Example 2 was performed to give 36.2 g of gallic acid-3,5-diglucoside in the form of while crystals. The purity was 96.2%. The corrected yield based on the purity was 70.5% (relative to GM).

EXAMPLE 5

To a reactor were fed 153.0 g (0.849 mol) of glucose (hereinafter referred to as "GLC"), 459 g of xylene, and 1.53 g (one percent by weight relative to the GLC) of sodium acetate as a catalyst, and then 520.3 g (5.09 mol) of acetic anhydride was added dropwise over a period of three hours at a temperature of 90° C. to 95° C. After the dropwise addition, the reaction was maintained at 105° C. for 14 hours. The reaction quantitatively proceeded. The conversion rate of the GLC was 100%. The resulting glucose pentaacetate was a mixture of α-PAG and β-PAG, the ratio of α-PAG to β-PAG being 2:8. After the reaction, acetic acid formed by the acylation in a reactor equipped with a distillation column having three to five theoretical plates was azeotropically distilled with the xylene. In fact, 1071 g of xylene was added to the mixture subjected to the acylation, and then 1546 g of an azeotropic mixture of xylene and acetic acid was distilled off at 45° C. to 55° C. under reduced pressure. The acetic acid in the distillate was 260.7. Only 0.1% of acetic acid relative to the amount of acetic acid formed by the acylation remained in the reaction mixture containing prepared PAG in the reactor.

To the resulting mixture containing the prepared PAG was added 8.0 g (15 mole percent relative to the GM) of a boron trifluoride-acetic acid complex as a catalyst, and acetic acid that originated from the catalyst was azeotropically distilled with xylene at 45° C. (22-24 mmHg), the distillation rate being 51 g/hr. After distillation, a slurry containing 52.1 g (0.283 mol) of GM and 52.2 g of xylene was quickly added while maintaining the conditions (at 45° C. (22-24 mmHg)), thus initiating the reaction. Acetic acid was azeotropically distilled with xylene while maintaining a distillation rate of 102 g/hr until three hours after starting the reaction. After three hours, the distillation rate was changed to 51 g/hr. Additional xylene was added at an amount of 112 g at intervals of one hour until three hours after starting the reaction. After three hours, the same amount of the additional xylene was added at intervals of two hours. During the reaction, 2.7 g (5 mole percent relative to the GM) of a boron trifluoride-acetic acid complex was each added at 6 and 12 hours after starting the reaction. The analysis of the reaction mixture indicated that the yield of gallic acid methyl ester-3,5-bis(2,3,4,6-tetra-O-acetylglucoside) was 90.5% relative to the GM. The concentration of acetic acid was 0.41 percent to 0.49 percent by weight in the reaction system during the reaction. The reaction mixture was cooled to room temperature while maintaining the reduced pressure. When the temperature was lowered to 20° C., the pressure was increased to atmospheric pressure. After aging for two hours, the crystal precipitate was filtered and washed twice with 78 g of xylene, followed by drying at 60° C. for 12 hours, to give 211.8 g of gallic acid methyl ester-3,5-bis(2,3,4,6-tetra-O-acetylglucoside) crystals. The purity was 95.4%. The corrected yield based on the purity was 84.5% (relative to GM).

Subsequently, the operation as in Example 2 was performed to give 100 g of gallic acid-3,5-diglucoside in the form of while crystals. The purity was 96.9%. The corrected yield based on the purity was 69.2%.

EXAMPLE 6

To a reactor were fed 11.03 g (0.1 mol) of hydroquinone (hereinafter referred to as "HQ"), 17.1 g (0.3 mol) of β-PAG, and 150 g of mixed xylenes, and then 2.1 g (15 mole percent relative to the HQ) of boron trifluoride diethyl etherate was added. The reaction was performed at a temperature of 43° C. to 47° C. under a pressure of 4.0 kPa to 3.6 kPa (30 mmHg to 27 mmHg) for 12 hours. The analysis of the reaction mixture indicated as follows: The yields of hydroquinone-1,4-bis(2,3,4,5-tetra-O-acetylglucoside), and hydroquinone-mono(2,3,4,5-tetra-O-acetylglucoside) were 89.0% and 10.0% relative to the HQ, respectively. Unreacted HQ content was 1.0%. The concentration of acetic acid was 0.45 percent to 0.50 percent by weight in the reaction system during the reaction.

COMPARATIVE EXAMPLE 1

To a reactor were fed 36.8 g (0.2 mol) of GM, 226.4 g (0.58 mol) of β-PAG, and 600 g of 1,2-dichloroethane, and then 4.4 g (15 mole percent relative to the GM) of boron trifluoride diethyl etherate was added. The reaction was performed at 50° C. Since the reaction did not proceed at four hours after starting the reaction, 2.0 g of boron trifluoride diethyl etherate functioning as a catalyst was further added. The reaction mixture was then maintained under the same conditions, but the reaction did not proceed. The yield of gallic acid methyl ester-3,5-bis(2,3,4,6-tetra-O-acetylglucoside) was 32.7%. The reaction mixture contained 7.1% (relative to the amount of fed GM) of the GM and 45% (relative to the GM) of gallic acid-3-(2,3,4,6-tetra-O-acetylglucoside). The concentration of acetic acid was 1.2 percent to 1.5 percent by weight in the reaction system during the reaction.

COMPARATIVE EXAMPLE 2

The same operation as in Examples was performed, but the distillation rate was about halved, as a result, the total weight of distillate was 240 g after 16 hours. The analysis of the reaction mixture indicated that the yields of gallic acid methyl ester-bis(2,3,4,6-tetra-O-acetylglucoside) and gallic acid methyl ester-mono(2,3,4,6-tetra-O-acetylglucoside) were 61.5% (relative to the GM) and 35% (relative to the GM), respectively. The concentration of acetic acid was 1.21 percent to 1.25 percent by weight in the reaction mixture during the reaction.

COMPARATIVE EXAMPLE 3

To a reactor were fed 11.03 g (0.1 mol) of HQ, 117.1 g (0.3 mol) of β-PAG, and 180 g mixed xylene, and then 2.1 g (15 mol percent relative to POB-Et) of boron trifluoride diethyl etherate was added. The reaction was performed at a temperature of 43° C. to 47° C. under atmospheric pressure for 20 hours. The analysis of the reaction mixture indicated that the yields of hydroquinone-1,4-bis(2,3,4,5-tetra-O-acetylglucoside) and hydroquinone-mono(2,3,4,5-tetra-O-acetylglucoside) were 38.5% (relative to the HQ) and 46.3% (relative to the HQ), respectively. The HQ as a starting material remained at only 4% relative to the fed HQ. The concentration of acetic acid was 1.6 percent to 1.8 percent by weight in the reaction system during the reaction.

INDUSTRIAL APPLICABILITY

The present invention can provide a method for preparing a glycoside with high yield, the glycoside being such that at least two phenolic hydroxyl groups of a compound having at least two phenolic hydroxyl groups in its molecule are glycosidically linked to anomeric carbon atoms of at least two sugar molecules.

The invention claimed is:

1. A method for preparing a glycoside represented by formula (3):

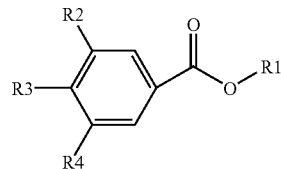

(3)

wherein:
R1 represents a $C_1$-$C_{10}$ straight or branched alkyl;
any one of R2, R3 and R4 represents a hydroxyl;
each of the remaining two of R2, R3, and R4 represent a residue formed by reacting glucose pentaacetate with a hydroxyl group of an alkyl gallate; and
the method comprises the step of:
reacting an alkyl gallate having a $C_1$-$C_{10}$ straight or branched alkyl with glucose pentaacetate in the presence of an organic solvent and an acid catalyst at 30° C. to 60° C. while removing from the reaction system organic solvent and acetic acid formed during the reaction, thereby maintaining the concentration of the acetic acid in the reaction system at 1.0 percent by weight or less during the reaction;
wherein a distillate comprising said acetic acid and organic solvent both removed from the reaction system is distilled off at a rate of 20 to 500 g/hr relative to one mol of the alkyl gallate having $C_1$-$C_{10}$ straight or branched alkyl; and
wherein an amount of the substrate concentration is 5 percent to 50 percent by weight.

2. The method for preparing a glycoside according to claim 1, wherein the organic solvent is xylene.

3. The method for preparing a glycoside according to claim 2, wherein the acid catalyst is a Lewis acid catalyst.

4. The method for preparing a glycoside according to claim 2, wherein the acid catalyst is boron trifluoride.

* * * * *